United States Patent
Cooper et al.

(10) Patent No.: US 8,556,915 B2
(45) Date of Patent: Oct. 15, 2013

(54) SKIN REMOVAL INSTRUMENT

(75) Inventors: Jennifer Z. Cooper, Lutherville, MD (US); Randolph E. Cooper, Lutherville, MD (US); Christopher J. Englert, Reisterstown, MD (US); Deborah A. Englert, Reisterstown, MD (US)

(73) Assignee: Derm Instruments & Innovations LLC, Lutherville, MD (US)

( * ) Notice: Subject to any disclaimer, the term of this patent is extended or adjusted under 35 U.S.C. 154(b) by 37 days.

(21) Appl. No.: 13/116,384

(22) Filed: May 26, 2011

(65) Prior Publication Data

US 2012/0303045 A1   Nov. 29, 2012

(51) Int. Cl.
*A61B 17/50* (2006.01)

(52) U.S. Cl.
USPC .......................................................... 606/131

(58) Field of Classification Search
USPC ................... 606/131, 210, 211, 133; D28/55; 294/99.2; 968/665, 666
See application file for complete search history.

(56) References Cited

U.S. PATENT DOCUMENTS

| | | | |
|---|---|---|---|
| 950,499 A | | 3/1910 | Wells |
| 1,286,673 A | * | 12/1918 | Linke ............................. 606/131 |
| 1,889,475 A | * | 11/1932 | Henkel ......................... 294/99.2 |
| 3,306,139 A | | 2/1967 | Brackett |
| 3,980,861 A | | 9/1976 | Fukunaga |
| 4,844,065 A | | 7/1989 | Faulkner |
| 5,334,215 A | | 8/1994 | Chen |
| 5,902,301 A | | 5/1999 | Olig |
| D456,097 S | | 4/2002 | LaMagna et al. |
| 6,471,515 B2 | * | 10/2002 | Feuer ............................. 433/162 |
| D506,573 S | | 6/2005 | de Grandcourt |
| 2006/0149300 A1 | | 7/2006 | Jessen et al. |
| 2008/0312669 A1 | | 12/2008 | Vries et al. |

FOREIGN PATENT DOCUMENTS

| | | |
|---|---|---|
| JP | 2002-142632 | 5/2002 |
| WO | 87-05483 | 9/1987 |

* cited by examiner

*Primary Examiner* — Ryan Severson
*Assistant Examiner* — Anh Dang
(74) *Attorney, Agent, or Firm* — Blank Rome LLP

(57) ABSTRACT

A skin removal instrument that comprises first and second resilient arms. Each of the first and second arms includes a main body that has a middle, an attachment end and a nipping end opposite the attachment end. The attachment ends are attached to one another, thereby forming a spring area that allows the nipping ends to resiliently move toward and away from each other. Each of the first and second arms includes an outer gripping area disposed offset from the middle of the main body of the first and second arms, respectively. The outer gripping area has a substantially bulbous shape. Each of the nipping ends of the first and second arms includes an extension portion that extends from the main body and a nipping blade portion that extends from the extension portion. Each of the nipping blade portions has an angled surface angled downwardly from an inner surface of the extension portions, respectively, such that the nipping blade portions converge toward one another. Each of the nipping blade portions includes a nipping edge at an end of the respective angled surface, wherein the nipping blade portions meet when the first and second arms are compressed together to remove a section of skin.

10 Claims, 4 Drawing Sheets

SKIN REMOVAL INSTRUMENT

FIELD OF THE INVENTION

The present invention relates to an instrument for removing skin. More specifically, the instrument is designed to safely and easily remove skin tags from the body.

BACKGROUND OF THE INVENTION

Skin tags are benign skin growths that look like small pieces of hanging skin on a stalk. Skins tags can form almost anywhere on the body where there is skin, especially in areas in friction, such as the neck, underarm and groin. Conventional methods for removing skin tags include destructive modalities, such as freezing the tag with liquid nitrogen, electrodessication, and use of a scalpel blade. There are several disadvantages to the current methods including discomfort to the patient and the time needed for the set up of the removal procedure.

Therefore, a need exists for a simple and easy mechanism for removing skin, particularly skin tags, without discomfort to the patient.

SUMMARY OF THE INVENTION

Accordingly, the present invention provides a skin removal instrument that comprises first and second resilient arms and each of the arms includes a main body that has a middle, an attachment end and a nipping end opposite the attachment end. The attachment ends of the arms are attached to one another, thereby forming a spring area that allows the nipping ends of the arms to resiliently move toward and away from each other. Each of the first and second arms includes an outer gripping area disposed offset from the middle of the main body of the arms, respectively. The outer gripping area has a substantially bulbous shape such that a width of the outer gripping area is substantially wider than a width of the remainder of the main body of each of the first and second arms. Each of the nipping ends of the first and second arms includes an extension portion that extends from the main body and a nipping blade portion that extends from the extension portion. Each of the nipping blade portions has an angled surface angled downwardly from an inner surface of the extension portions, respectively, such that the nipping blade portions converge toward one another. Each of the nipping blade portions includes a nipping edge at an end of the respective angled surface, wherein the nipping blade portions meet when the first and second arms are compressed together to remove a section of skin. In one exemplary embodiment, the nipping edges are rounded.

The present invention may also provide a skin removal instrument that comprises first and second resilient arms that have an elongated main body that is curved backwardly along a length thereof. The main body of each of the first and second arms includes a middle, an attachment end and a nipping end opposite the attachment end. The attachment ends of the first and second arms are attached to one another, thereby forming a spring area that allows the nipping ends of the arms to resiliently move toward and away from each other. Each of the first and second arms includes an outer gripping area disposed offset from the middle of the main body of the first and second arms, respectively. The outer gripping area has a substantially bulbous shape such that a width of the outer gripping area is substantially wider than a width of the remainder of the main body of each of the first and second arms. The outer gripping area includes a plurality of uniformly spaced parallel grooves. Each of the nipping ends of the first and second arms includes an extension portion that extends forwardly from the main body. A bottom surface of each of the extension portions is substantially flat. A nipping blade portion extends inwardly from the extension portion. A bottom surface of each of the nipping blade portions is substantially co-planar with the respective bottom surfaces of the extension portions. Each of the nipping blade portions has an angled surface angled downwardly from an inner surface of the extension portions, respectively, such that the nipping blade portions converge toward one another. Each of the nipping blade portions including a nipping edge at an end of the respective angled surface. Each of the nipping edges is rounded, wherein the nipping blade portions meet when the first and second arms are compressed together to remove a section of skin.

The present invention may also provide a skin removal instrument that comprises first and second resilient arms and each of the first and second arms is curved. The first and second resilient arms are attached at one end. A means for gripping is disposed on an outer surface of each of the first and second arms, respectively. A means for nipping is disposed on the other end of each of the first and second arms, respectively, for removing skin.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EXEMPLARY EMBODIMENTS

Figure 1:
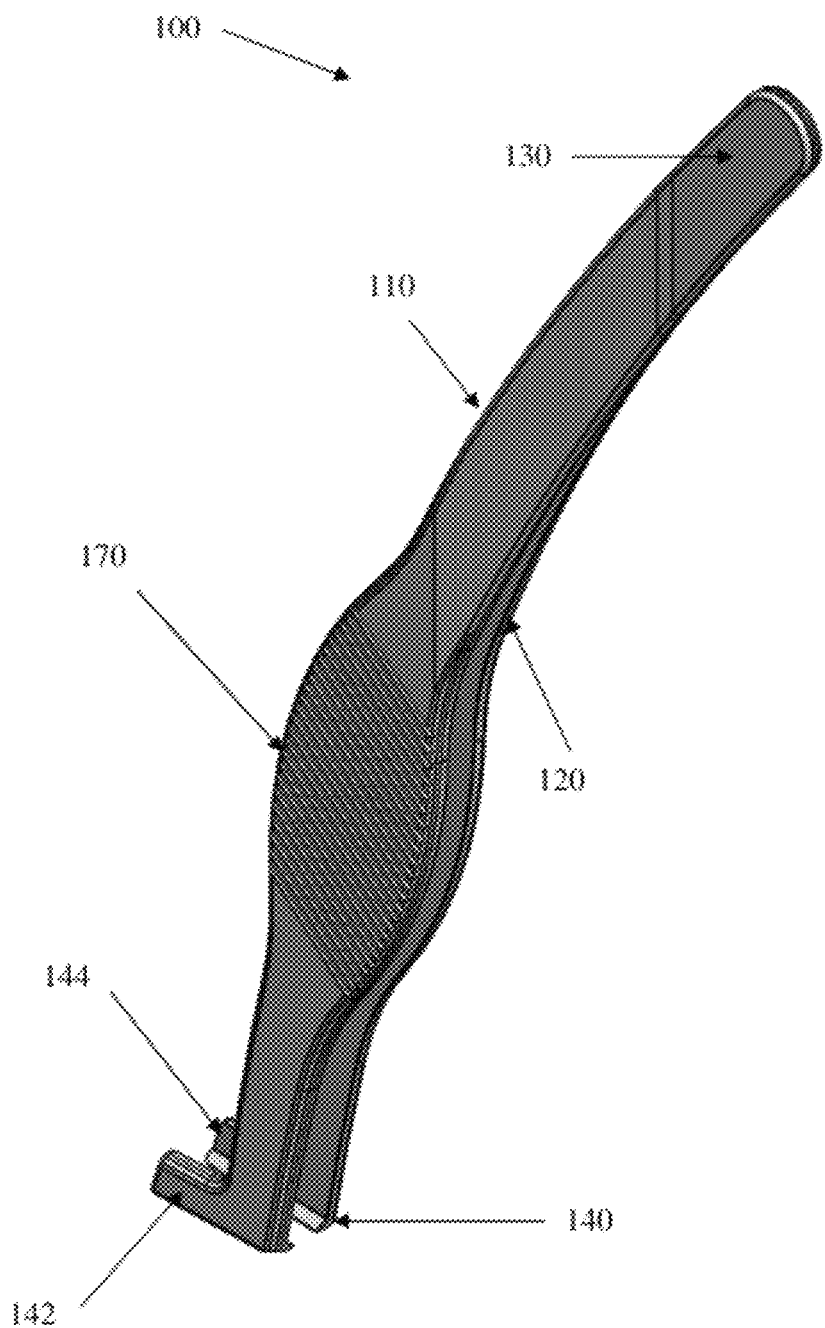
FIG. 1 is a rear, side perspective view of a removal instrument according to an exemplary embodiment of the invention.

Referring to FIGS. 1-5, a skin removal instrument 100 according to an exemplary embodiment of the present invention generally includes first and second arms 110 and 120 that each has an attachment end 130 where the arms 110 and 120 are attached together and an opposite nipping end 140 that is configured to cut or remove skin, such as a skin tag, by pinching off the skin. The instrument effectively removes the skin tag by compressing the skin tag stalk until the nipping ends 140 meet, thereby separating the skin tag stalk from the body.

Figure 2:
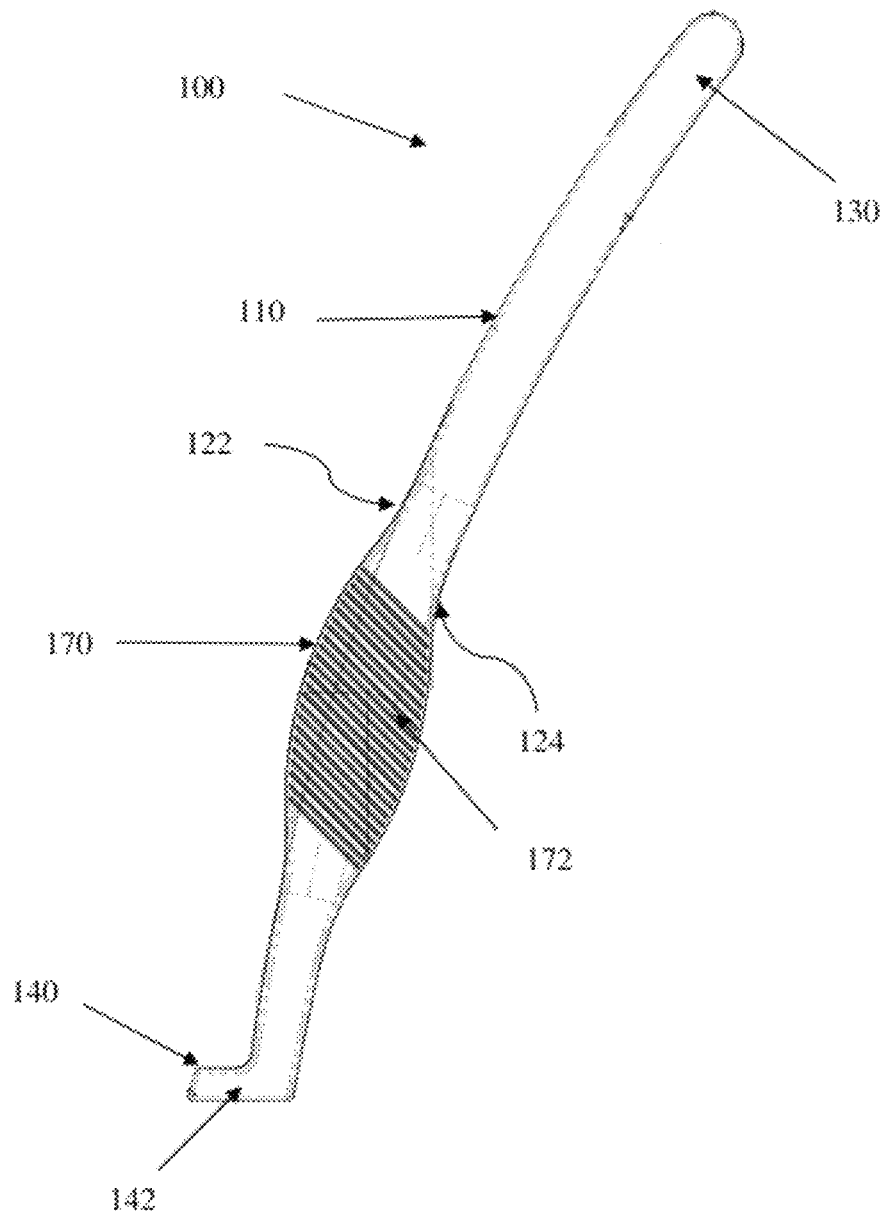
FIG. 2 is a side elevational view of the removal instrument illustrated in FIG. 1.

As best seen in FIGS. 1 and 2, each of the arms 110 and 120 has a main body that may be elongated and substantially flat. Each main body of the arms 110 and 120 preferably curves backwardly, that is away from the front of the instrument 100, thereby defining opposite edges 122 and 124 that are substantially continuously curved without any flat sections, as seen in FIG. 2. That curved design provides multiple gripping positions, such as overhand or underhand, because the curved nature of the arms 110 and 120 facilitates support of the instrument 100 in the operator's hand and fingers regardless of the orientation of the instrument, such as upright or upside down. That is particularly useful when the operator is using the instrument 100 to remove skin from his or her own body and may need to position the instrument 100 in a particular orientation. The curved design also provides enhanced ergonomics to the instrument 100.

Each arm 110 and 120 may be formed of a resilient material, such as stainless steel and the like. The arms 110 and 120 may also be formed of a resilient hard plastic. Because of the resilient nature the arms 110 and 120, a spring area is formed where the arm attachment ends 130 meet so that the arms 110 and 120 can resiliently move toward and away from each other when compressed.

The nipping ends 140 of the arms 110 and 120 include an extension portion 142 and 144, respectively. Each extension portions 142 and 144 extends forwardly from the main bodies of arms 110 and 120, respectively, to form substantially L-shaped ends, as seen in FIG. 2 (showing extension portion 142 of arm 110). Each extension portion 142 and 144 has a bottom surface 158 that may be substantially flat such that the bottom surfaces are generally aligned with one another, as seen in FIG. 5.

Figure 3:
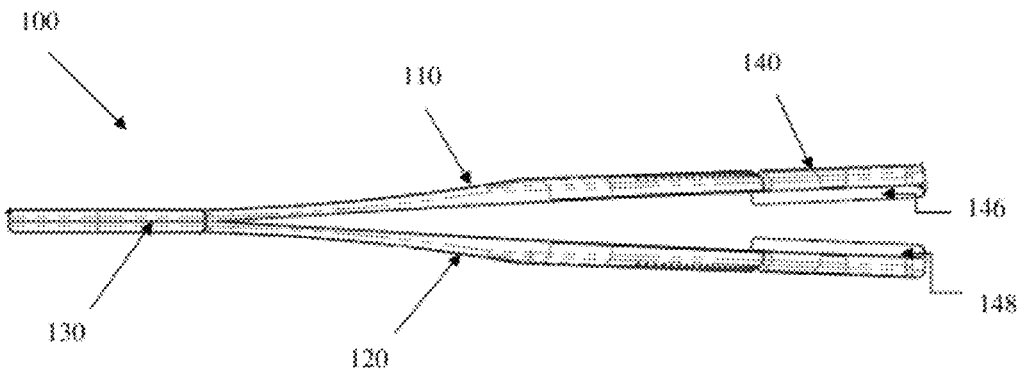
FIG. 3 is a top view of the removal instrument illustrated in FIG. 1.
Figure 4:
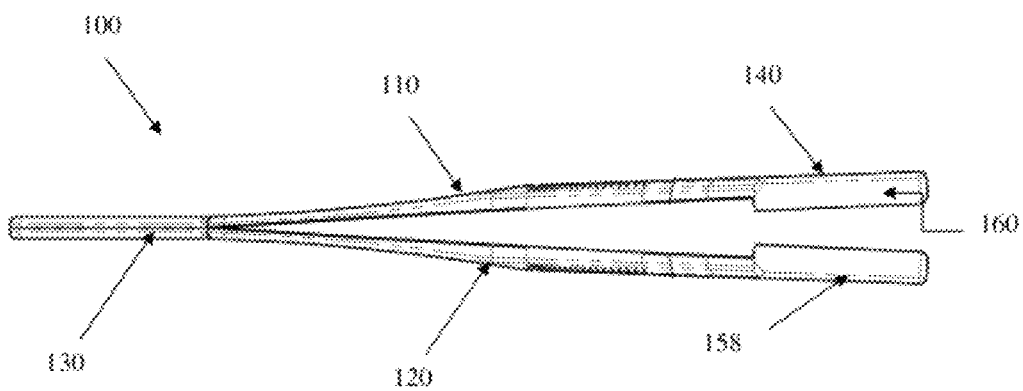
FIG. 4 is a bottom view of the removal instrument illustrated in FIG. 1.

Each extension portion 142 and 144 of the nipping ends 140 includes an inwardly extending nipping blade portion 146 and 148, respectively, as seen in FIGS. 3 and 4. Each nipping blade portion 146 and 148 has a bottom surface 160 that may be substantially flat and generally co-planar with the bottom surfaces of the extension portions 142 and 144, as seen in FIG. 5. Each nipping blade portion 146 and 148 defines a downwardly angled surface 150 and 152, respectively, such that the nipping blade portions 146 and 148 converge toward one another defining an area 162 (FIG. 5) configured to receive a portion of skin, such as a skin tag.

Figure 5:
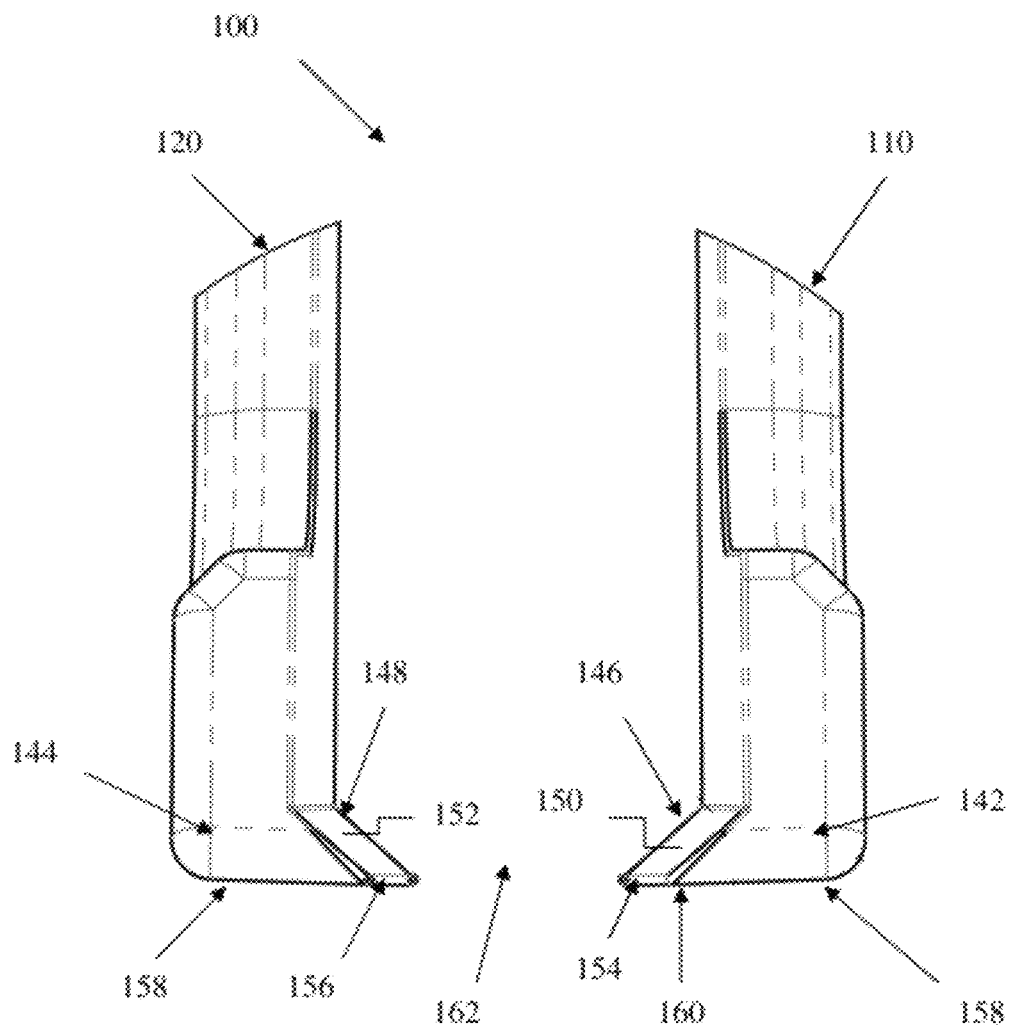
FIG. 5 is an enlarged partial elevational view of the removal instrument illustrated in FIG. 1.

As seen in FIG. 5, each nipping blade portion 146 and 148 includes a nipping edge 154 and 156, respectively, at the ends of the angled surfaces 150 and 152. The nipping edges 154 and 156 are configured to pinch off and remove skin by concentrating the force applied to the arms 110 and 120 on a relatively small area of the skin, such as the stalk of a skin tag. As seen in FIG. 4, the nipping edges of the ends 140 are substantially parallel to one another. The nipping edges 154 and 156 are preferably rounded or blunt. The roundness of the edges 154 and 156 allows the skin tag stalk to be compressed and pinched off or removed with minimal or no bleeding to the skin area. The roundness of the edges 154 and 156 also prevents the operator of the instrument from grabbing a section of skin and slicing into it. Although it is preferably that the nipping edges 154 and 156 be rounded, one or more of the edges 154 and 156 may be sharp to provide a cutting edge if desired.

An outer gripping area 170 is provided on an outer surface of each of the arms 110 and 120, as seen in FIGS. 1 and 2 (showing the outer gripping area 170 on arm 110). The outer gripping area 170 is positioned such that it is offset from the middle of each arm. That is, the outer gripping area 170 is located closer to the nipping ends 140 of each arm 110 and 120 than to the attachment ends 130. As seen in FIG. 2, the outer gripping area 170 preferably has a substantially bulbous shape such that it defines a width that is larger than the width of the remainder of the arm to provide sufficient surface area for grasping the instrument 100. The outer gripping area 170 preferably includes plurality of uniformly spaced parallel grooves 172 to facilitate gripping of each arm 110 and 120. Although grooves 172 are preferred, any known gripping surface may be used such as knurls or detents.

While a particular embodiment has been chosen to illustrate the invention, it will be understood by those skilled in the art that various changes and modifications can be made therein without departing from the scope of the invention as defined in the appended claims.

What is claimed is:

1. A skin removal instrument, comprising:
   first and second resilient arms, each of said first and second arms including a main body having a middle, an attachment end and a nipping end opposite said attachment end, said attachment ends of said first and second arms being attached to one another, thereby forming a spring area allowing said nipping ends of said first and second arms to resiliently move toward and away from each other,
   each of said first and second arms including an outer gripping area disposed offset from said middle of said main body of said first and second arms, respectively, said outer gripping area having a substantially bulbous shape such that a width of said outer gripping area is substantially wider than a width of the remainder of said main body of each of said first and second arms, and
   each of said nipping ends of said first and second arms including an extension portion that extends from said main body and a nipping blade portion that extends from said extension portion, each of said nipping blade portions having an angled surface angled downwardly from an inner surface of said extension portions, respectively, such that said nipping blade portions converge toward one another, and each of said nipping blade portions including a nipping edge at an end of said respective angled surface, said nipping edges always being parallel to each other, wherein said nipping blade portions meet and said nipping edges meet when said first and second arms are compressed together to remove a section of skin.

2. A skin removal instrument according to claim 1, wherein each of said main bodies includes opposite edges that are continuously curved without any flat sections.

3. A skin removal instrument according to claim 1, wherein each of said nipping edges is rounded.

4. A skin removal instrument according to claim 1, wherein said outer gripping area includes a plurality of uniformly spaced parallel grooves.

5. A skin removal instrument according to claim 1, wherein a bottom surface of each of said extension portions is substantially co-planar with a bottom surface of each of said nipping blade portions, respectively.

6. A skin removal instrument according to claim 5, wherein
   said bottom surfaces of said extension portions and said nipping blade portions extend from said nipping edges to outer surfaces of extension portions,
   said bottom surfaces of said extension portions and said nipping blade portions are substantially flat.

7. A skin removal instrument according to claim 1, wherein each of said main bodies curves backwardly along a length thereof; and
   each of said extension portions extend forwardly from each of said main bodies, respectively.

8. A skin removal instrument according to claim 1, wherein each of said nipping blade portions extends inwardly from an inner surface of each of said extension portions, respectively.

9. A skin removal instrument according to claim 1, wherein said first and second arms are formed of stainless steel or a hard plastic.

10. A skin removal instrument, comprising:

first and second resilient arms, each of said first and second arms including a main body having a middle, an attachment end and a nipping end opposite said attachment end, said attachment ends of said first and second arms being attached to one another, thereby forming a spring area allowing said nipping ends of said first and second arms to resiliently move toward and away from each other, and each of said first and second arms including an outer gripping area, disposed offset from said middle of said main body of said first and second arms, respectively and each of said nipping ends of said first and second arms including an extension portion that extends from said main body and a nipping blade portion that extends from said extension portion, each of said nipping blade portions having an angled surface angled from an inner surface of said extension portions, respectively, such that said nipping blade portions converge toward one another, and each of said nipping blade portions including a nipping edge at a free end of said respective angled surface, said nipping edges always being parallel to each other, wherein said nipping blade portions meet and said nipping edges meet when said first and second arms are compressed together to remove a section of skin.

* * * * *